US007767160B2

(12) United States Patent
Sasaki et al.

(10) Patent No.: US 7,767,160 B2
(45) Date of Patent: Aug. 3, 2010

(54) APPARATUS FOR CONTINUOUSLY PRODUCING POLYISOCYANATE

(75) Inventors: Masaaki Sasaki, Kamisu (JP); Kouji Maeba, Kamisu (JP); Mitsunaga Douzaki, Kamisu (JP); Hirofumi Takahashi, Kamisu (JP); Osamu Hososaka, Minato-ku (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 310 days.

(21) Appl. No.: 11/887,583

(22) PCT Filed: Mar. 30, 2006

(86) PCT No.: PCT/JP2006/306633

§ 371 (c)(1), (2), (4) Date: Oct. 1, 2007

(87) PCT Pub. No.: WO2006/109576

PCT Pub. Date: Oct. 19, 2006

(65) Prior Publication Data

US 2009/0081086 A1 Mar. 26, 2009

(30) Foreign Application Priority Data

Apr. 5, 2005 (JP) ............................ 2005-108590

(51) Int. Cl.
*B01J 19/18* (2006.01)
*C07C 211/00* (2006.01)

(52) U.S. Cl. ....................... 422/132; 422/105; 422/131; 564/330; 560/347

(58) Field of Classification Search ................. 422/105, 422/131, 132; 564/330; 560/347
See application file for complete search history.

(56) References Cited

U.S. PATENT DOCUMENTS 2,822,373 A 2/1958 Beck (Continued)

FOREIGN PATENT DOCUMENTS

GB 1255637 12/1971

(Continued)

OTHER PUBLICATIONS

International Preliminary Report on Patentability and Written Opinion issued in corresponding International Patent Application No. PCT/JP2006/306633; Oct. 18, 2007; The International Bureau of WIPO, Geneva, CH.

*Primary Examiner*—Walter D Griffin
*Assistant Examiner*—Huy-Tram Nguyen
(74) *Attorney, Agent, or Firm*—Buchanan Ingersoll & Rooney PC

(57) ABSTRACT

An apparatus for continuously producing polyisocyanate is provided for quickly contacting polyamine and carbonyl chloride in order to suppress an undesirable reaction between polyamine and polyisocyanate so that a by-product can be reduced and the yield of polyisocyanate can be improved. In a circulatory line 7, a material-mixing portion 8, a high-shear pump 3, a reactor 4, a liquid-feeding pump 5 and a cooler 6 are interposed in series along the direction of the flow of a reaction solution, thereby forming a closed line. In this apparatus 1, after polyamine and carbonyl chloride are supplied in the material-mixing portion 8, the reaction solution is sheared by the high-shear pump 3 in a state where the contact of the polyamine with the reaction solution is minimized. Thus, the formation of a urea compound as a by-product can be suppressed and the yield of polyisocyanate can be improved.

10 Claims, 2 Drawing Sheets

U.S. PATENT DOCUMENTS 3,381,025 A * 4/1968 Mitsumori et al. .......... 560/347
3,781,320 A 12/1973 Irwin
3,801,518 A * 4/1974 Irwin et al. ................. 521/126
4,128,569 A 12/1978 Horn et al.
4,289,732 A * 9/1981 Bauer et al. ................. 422/224
4,422,976 A 12/1983 Yamamoto et al.
6,433,219 B1 * 8/2002 Strofer et al. ............... 560/347
6,706,913 B2 * 3/2004 Leimkuhler et al. ......... 560/347
6,831,192 B2 * 12/2004 Strofer et al. ............... 560/347
6,896,401 B2 * 5/2005 Wolfert et al. ........... 366/162.4
6,930,199 B2 * 8/2005 Meyn et al. ................. 560/347
7,230,130 B2 * 6/2007 Strofer et al. ............... 560/347
2003/0013909 A1 * 1/2003 Leimkuhler et al. ......... 560/347
2003/0069441 A1 * 4/2003 Leimkuhler et al. ......... 560/347
2005/0137417 A1 * 6/2005 Meyn et al. ................. 560/347
2007/0175333 A1 * 8/2007 Shoemaker et al. ........... 96/243

FOREIGN PATENT DOCUMENTS

GB 1255638 12/1971
JP 35-10774 B1 8/1960
JP 45-1447 B1 1/1970
JP 57-048954 A 3/1982
JP 57-165358 A 10/1982
JP 2004-035492 A 2/2004

* cited by examiner

APPARATUS FOR CONTINUOUSLY PRODUCING POLYISOCYANATE

TECHNICAL FIELD

The present invention relates to an apparatus for continuously producing polyisocyanate to be used as a raw material of polyurethane.

BACKGROUND ART

Polyisocyanate used as a raw material of polyurethane has been industrially produced by reacting polyamine with carbonyl chloride for an isocyanate reaction.

Such polyisocyanate has been industrially produced by continuously supplying a polyamine solution including polyamine, a carbonyl chloride solution containing carbonyl chloride, and a solvent to a reactor, reacting them so as to generate polyisocyanate, and continuously distilling the generated polyisocyanate (see the following Patent Document 1).

When polyamine and carbonyl chloride are directly supplied to a reactor so as to be reacted, a reaction temperature rises so that a side reaction easily generates. Thus, a following technique to obtain polyisocyanate effectively has been known, that is, the technique by the steps of circulating a portion of a reaction solution distilled from a reactor in the reactor again, supplying polyamine and carbonyl chloride to its circulatory line, reacting them at low temperature by a cooling device interposed in the circulatory line, and reacting a resulting reaction solution at high temperature (see the following Patent Document 2).

Patent Document 1: Japanese Unexamined Patent Publication No. 2004-035492)

Patent Document 2: Japanese Unexamined Patent Publication No. 57-165358)

DISCLOSURE OF THE INVENTION

Problems to be Solved by the Invention

However, in a reaction of polyamine and carbonyl chloride, carbamoyl chloride rapidly generates when polyamine contacts to carbonyl chloride. Subsequently, the carbamoyl chloride is gradually converted to isocyanate. Since carbamoyl chloride is hardly dissolved in an organic solvent, a slurry is generated when polyamine contacts to carbonyl chloride in the organic solvent.

On other hand, when polyamine and carbonyl chloride are supplied to a circulatory line of a reaction solution, polyamine is reacted with polyisocyanate in the circulating reaction solution. Thus, a urea compound as a by-product is produced, and a yield of polyisocyanate decreases.

Therefore, it is necessary to quickly contact between polyamine and carbonyl chloride supplied to the circulatory line so as to generate a uniform slurry of carbamoyl chloride.

An object of the present invention is to provide an apparatus for continuously producing polyisocyanate by supplying polyamine and carbonyl chloride and quickly contacting them to suppress an undesirable side reaction between polyamine and polyisocyanate, which can reduce a by-product and improve the yield of polyisocyanate.

Solution to the Problems

In order to achieve the above-described object, the apparatus for continuously producing polyisocyanate by reacting polyamine with carbonyl chloride of the present invention comprises a reactor and a circulatory means for circulating a reaction solution to the reactor, the circulatory means comprising:

1) a circulatory line for circulating the reaction solution,
2) polyamine supplying means for supplying polyamine to the circulatory line,
3) carbonyl chloride supplying means for supplying carbonyl chloride to the circulatory line,
4) polyamine-carbonyl chloride contacting means for contacting the polyamine supplied from the polyamine supplying means to the circulatory line and the carbonyl chloride supplied from the carbonyl chloride supplying means to the circulatory line in the presence of the circulating reaction solution, and
5) mixing means for mixing the carbonyl chloride and the polyamine contacted by the contacting means, and the circulated reaction solution by shearing.

In the apparatus, polyamine and carbonyl chloride are supplied to the circulatory means by the polyamine supplying means and the carbonyl chloride means, and contact each other in the presence of a circulating reaction solution by the contacting means. Next, the contacted carbonyl chloride and the polyamine are mixed with the circulating reaction solution by the mixing means by shearing. Since the polyamine and the carbonyl chloride becomes fine liquid droplets by shearing and then contact each other in the reaction solution, a uniform slurry of the carbamoyl chloride and polyamine hydrochloride can be quickly produced. Therefore, a reaction of the polyisocyanate and the polyamine in the circulating reaction solution can be suppressed, and thus a formation of a urea compound as a by-product can be reduced, and the yield of polyisocyanate can be improved.

Further, in the apparatus, it is preferable that the polyamine supplied from the polyamine supplying means to the circulatory line and the polyisocyanate in the circulated reaction solution are not substantially reacted in the circulatory means.

When the polyamine supplied from the polyamine supplying means to the circulatory line and the polyisocyanate in the circulating reaction solution are not substantially reacted, a urea compound as a by-product is not substantially formed, and the yield of polyisocyanate can be more improved.

Further, in the apparatus, it is preferable that a distance between the contacting means and the mixing means is 1,000 mm or less.

When the distance between the contacting means and the mixing means is excessively long, a chance increases that the circulating reaction solution in the circulatory line contacts to the polyamine supplied from the polyamine supplying means to the circulatory line by turbulently mixing to promote the formation of a urea compound as a by-product.

However, when the distance between the contacting means and the mixing means is 1,000 mm or less, the chance can be reduced that the circulating reaction solution within the circulatory line contacts to the polyamine supplied from polyamine supplying means to the circulatory line by turbulently mixing. Thus, the formation of a urea compound as a by-product can be more suppressed.

Further, in the apparatus, it is preferable that a linear velocity of the polyamine supplied from the polyamine supplying means to the circulatory line is from 0.5 to 10 m/sec in a cross section of the polyamine supplying means. Further, it is preferable that a linear velocity of the carbonyl chloride supplied from the carbonyl chloride supplying means to the circulatory line is from 0.5 to 10 m/sec in a cross section of the carbonyl chloride supplying means. Furthermore, it is preferable that a linear velocity of the reaction solution within the circulatory line immediately before supplying to the contacting means is from 0.3 to 5 m/sec.

In the apparatus, when the linear velocity of the polyamine in a cross section of the polyamine supplying means is from 0.5 to 10 m/sec, the linear velocity of the carbonyl chloride in a cross section of the carbonyl chloride supplying means is from 0.5 to 10 m/sec, and the linear velocity of the reaction solution within the circulatory line is from 0.3 to 5 m/sec, the yield of polyisocyanate can be improved.

On the other hand, in the apparatus, it is preferable that the polyamine supplied from the polyamine supplying means, the carbonyl chloride supplied from the carbonyl supplying means, and the reaction solution substantially form three layers from the contacting means to the mixing means.

Between the contacting means and the mixing means, when the polyamine supplied from the polyamine supplying means, the carbonyl chloride supplied from the carbonyl supplying means, and the reaction solution substantially form three layers, the contacting chance of the polyamine supplied from the polyamine supplying means to the polyisocyanate in the reaction solution can be reduced.

Further, in the apparatus, it is preferable that the polyamine supplying means comprises a polyamine supplying line having a flow-out side end portion that is inserted into the circulatory line, and the carbonyl chloride supplying means comprises a carbonyl chloride supplying line having a flow-out side end portion that is inserted into the circulatory line. Further, it is preferable that the flow-out side end portion of the polyamine supplying line is provided adjacent to an inner wall surface of the circulatory line and opens toward a downstream side with respect to a flow of the reaction solution from the contacting means to the mixing means, and that the flow-out side end portion of the carbonyl chloride supplying line opens toward a flow-out solution of the polyamine supplied from the flow-out side end portion of the polyamine supplying line.

The flow-out side end portion of the polyamine supplying line is provided adjacent to the inner wall surface of the circulatory line and opens toward the downstream side with respect to the flow of the reaction solution from the contacting means to mixing means, and the flow-out side end portion of the carbonyl chloride supplying line opens toward the flow-out solution of the polyamine supplied from the flow-out side end portion of the polyamine supplying line. In such a structure, the flow-out solution of the polyamine supplied from the polyamine supplying line is covered with the inner wall surface of the circulatory line and the carbonyl chloride supplied from the flow-out side end portion of the carbonyl chloride supplying line. Thus, the contact of the flow-out solution of the polyamine with the reaction solution can be suppressed so that the reaction of the polyisocyanate in the reaction solution and the supplied polyamine can be suppressed. Therefore, the yield of polyisocyanate can be improved.

Further, in the apparatus, it is preferable that a cooling device is interposed in a middle of the circulatory line and a temperature of the reaction solution after supplying the polyamine and the carbonyl chloride within the circulatory line is controlled to 120° C. or lower.

When the temperature of a reaction solution after supplying the polyamine and the carbonyl chloride within the circulatory line is 120° C. or lower, the formation of a urea compound as a by-product can be more suppressed.

Effect of the Invention

An apparatus for continuously producing polyisocyanate of the present invention can suppress reacting polyisocyanate in a circulated reaction solution and polyamine, reduce forming a urea compound as a by-product, and improve the yield of polyisocyanate.

DESCRIPTION OF REFERENCE NUMERALS

1: Apparatus for continuously producing polyisocyanate
2: Circulatory portion
3: High-shear pump
4: Reactor
7: Circulatory line
8: Material-mixing portion
9: Polyamine supplying line
10: Carbonyl chloride supplying line
11: Flow-in side end portion of the polyamine supplying line
12: Opening portion of the polyamine supplying line
13: Flow-in side end portion of the carbonyl chloride supplying line
14: Opening portion of the carbonyl chloride supplying line

EMBODIMENTS OF THE INVENTION

Figure 1:
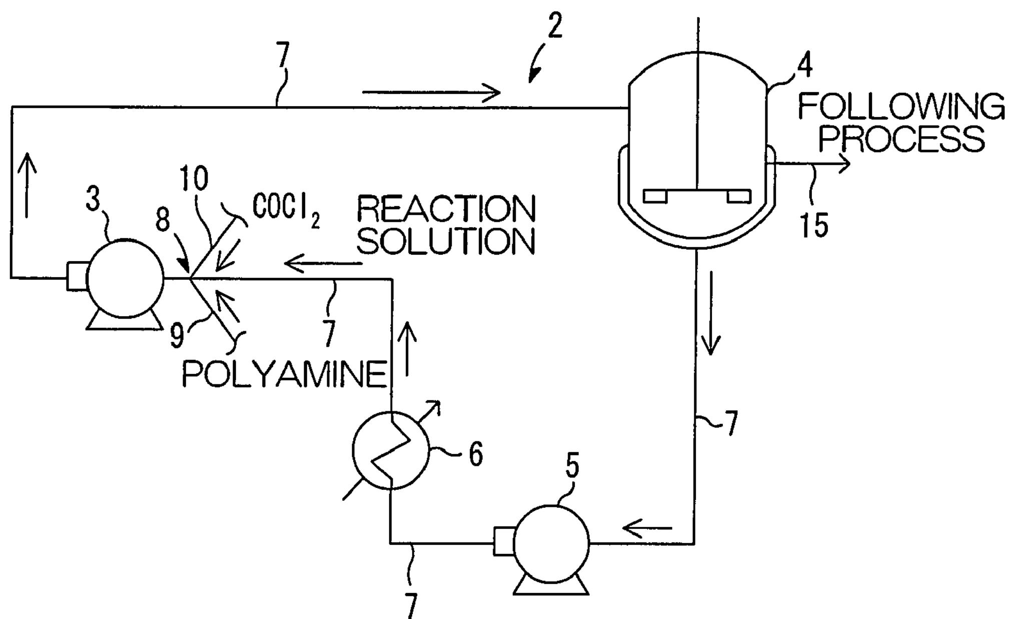
FIG. 1 is a schematic block diagram showing an embodiment of an apparatus for continuously producing polyisocyanate.

FIG. 1 is a schematic block diagram showing an embodiment of an apparatus for continuously producing polyisocyanate.

In FIG. 1, an apparatus continuously producing polyisocyanate 1 has a structure of a low temperature reaction type apparatus, and includes a reactor 4 as a reactor, and a circulatory portion 2 as circulatory means for circulating a reaction solution to the reactor 4.

The circulatory portion 2 includes a circulatory line 7, a material-mixing portion 8 as contacting means, a polyamine supplying line 9 as polyamine supplying means, a carbonyl chloride supplying line 10 as carbonyl chloride supplying means, a high-shear pump 3 as mixing means, a liquid-feeding pump 5, and a cooler 6 as a cooling device.

The circulatory line 7 is formed as a closed line so that its upstream side end portion and its downstream side end portion are connected with the reactor 4 so as to circulate a reaction solution to the reactor 4 (hereinafter "upstream side" and "downstream side" are based on a flow direction of the reaction solution unless otherwise specified).

The material-mixing portion 8 is adapted as a portion of the circulatory line 7 connected with the polyamine supplying line 9 and the carbonyl chloride supplying line 10.

The polyamine supplying line 9 is made of a steel tube having corrosion resistance to transport polyamine. Its flow-in side end portion is connected with a polyamine storage tank for storing polyamine, which is not shown, and its flow-out side end portion 11 is connected with the material-mixing portion 8.

Figure 2:
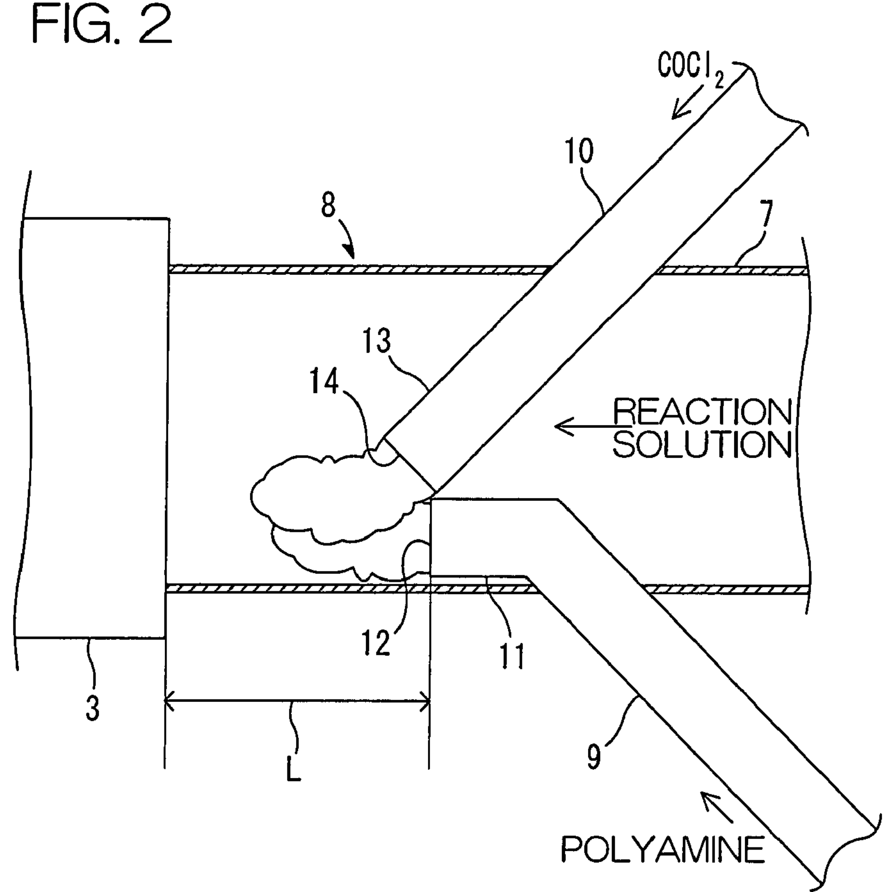
FIG. 2 is a schematic block diagram showing a material-mixing portion of the apparatus for continuously producing polyisocyanate shown in FIG. 1.

More particularly, as shown in FIG. 2, the polyamine supplying line 9 is provided adjacent to the circulatory line 7 so as to incline at the flow-out side end portion 11 to be gradually closer to the circulatory line 7, and the flow-out side end portion 11 is inserted into the circulatory line 7 from one side of the circulatory line 7 while inclining. Further, the flow-out side end portion 11 is formed so as to be bent toward the downstream side along the direction of the flow of a reaction solution (circulating direction), and is provided adjacent to an inner wall surface of one side within the circulatory line 7. Accordingly, an opening portion 12 of the polyamine supplying line 9 opens toward the downstream side.

The carbonyl chloride supplying line 10 is made of a steel tube having corrosion resistance to transport carbonyl chloride. Its flow-in side end portion is connected with a carbonyl chloride storage tank for storing carbonyl chloride, which is not shown, and its flow-out side end portion 13 is connected with the material-mixing portion 8.

More particularly, the carbonyl chloride supplying line 10 is provided on the other side which is the opposite side to the polyamine supplying line 9 with respect to the circulatory line 7. The carbonyl chloride supplying line 10 is provided adjacent to the circulatory line 7 so as to incline at the flow-out side end portion 13 to be gradually closer to the circulatory line 7, and the flow-out side end portion 13 side is inserted into the circulatory line 7 from the other side of the circulatory line 7 while inclining. In addition, the position at which the carbonyl chloride supplying line 10 is inserted into the circulatory line 7 is arranged to be opposite to the position where the polyamine supplying line 9 is inserted into the circulatory line 7 in the diameter direction of the circulatory line 7.

Further, the flow-out side end portion 13 of the carbonyl chloride supplying line 10 is inclined with respect to the direction of the flow of a reaction solution, and then is straightly extended. An opening portion 14 of the flow-out side end portion 13 is provided adjacent to the opening portion 12 of the polyamine supplying line 9 so as to open toward a flow-out solution of polyamine supplied from the opening portion 12 of the polyamine supplying line 9. More particularly, it is preferable that the opening portion 14 of the carbonyl chloride supplying line 10 is provided on the other side of the opening portion 12 of the polyamine supplying line 9, one end portion in the diameter direction of the opening portion 14 of the carbonyl chloride supplying line 10 is provided adjacent to or slightly more on the upstream side than the opening portion 12 of the polyamine supplying line 9, and the other end portion in the diameter direction of the opening portion 14 of the carbonyl chloride supplying line 10 is provided more on the downstream side than the opening portion 12 of the polyamine supplying line 9.

As shown in FIG. 1, the high-shear pump 3 is interposed in the circulatory lines at the downstream side of the material-mixing portion 8, and is not specifically limited as long as the pump can highly disperse a slurry (slurry of carbamoyl chloride generated by contacting polyamine with carbonyl chloride, and polyamine hydrochloride) in the reaction solution by a shearing force. For example, a centrifugal pump or a rotary pump can be used.

The centrifugal pump highly shears the slurry by rotating an impeller at high speed in a casing. It is preferable to use a canned pump as a centrifugal pump.

The rotary pump highly shears the slurry by rotating a gear, a partition plate or a screw at high speed in a casing. It is preferable to use a gear pump as a rotary pump.

Although the revolving speed of the high-shear pump 3 can be properly set, for example, it is 1,000 to 5,000 $min^{-1}$.

Further, the high-shear pump 3 is arranged to have a distance L from the opening portion 12 of the flow-out side end portion 11 of the polyamine supplying line 9 being 1,000 mm or less, preferably 500 mm or less, and more preferably 250 mm or less. When the distance L is larger than that, a chance may increase that a reaction solution circulated within the circulatory line 7 contacts with polyamine supplied from the polyamine supplying line 9 to the circulatory line 7 by turbulently mixing so as to promote production of a urea compound as a by-product. When the distance L is smaller than that, the contact of a reaction solution circulated within the circulatory line 7 with polyamine supplied from the polyamine supplying line 9 to the circulatory line 7 by turbulently mixing can be reduced to suppress a formation of a urea compound as a by-product.

The reactor 4 is interposed in the circulatory line 7 at the downstream side of the high-shear pump 3. The reactor is not specifically limited as long as it can react supplied polyamine and carbonyl chloride for an isocyanate reaction. For example, a continuous reactor having a stirring blade can be used. Further, it is preferable that the reactor 4 is constructed as a multistage type. In this case, the reactor 4 shown in FIG. 1 is a reactor of a first stage, and a reactor of a second stage, which is not shown, is connected in the following process.

The liquid-feed pump 5 is interposed in the circulatory line 7 at the downstream side of the reactor 4. The liquid-feed pump 5 is not specifically limited as long as it can transport the reaction solution. For example, the centrifugal pump and the rotary pump, and further a reciprocating pump can be used.

The cooler 6 is interposed in the circulatory line 7 at the downstream side of the liquid-feed pump 5 (the discharging side of the liquid-feed pump 5). The cooler 6 is not specifically limited as long as it can cool the reaction solution. For example, a heat exchanger in which a refrigerant (cooling water) is circulated can be used.

The cooler 6 is to cool a reaction solution after supplying polyamine and carbonyl chloride so that a temperature of the reaction solution is 120° C. or lower.

Then, a circulatory portion 2 includes the material-mixing portion 8, the high-shear pump 3, the reactor 4, the liquid-feed pump 5, and the cooler 6 in series along the direction of the flow of a reaction solution within the circulatory line 7 as described above, and the reaction solution within the circulatory line 7 circulates in the foregoing.

In the apparatus for continuously producing polyisocyanate 1, polyamine is supplied from the polyamine supplying line 9 to the material-mixing portion 8, and carbonyl chloride is supplied from the carbonyl chloride supplying line 10 to the material-mixing portion 8, in the material-mixing portion 8.

Polyamine is stored as it is or by prepared as a polyamine solution in a polyamine storage tank. The polyamine solution can be prepared by dissolving polyamine with an organic solvent. On the other hand, when polyamine is stored as it is, the polyamine is mixed at an organic solvent mixing portion provided at the polyamine supplying line 9 so as to be prepared as a polyamine solution. The polyamine solution is supplied from the polyamine supplying line 9 to the material-mixing portion 8.

Polyamine corresponds to polyisocyanate used in a production of polyurethane and is not specifically limited. For example, polyamine is properly selected from an aromatic diamine, e.g., polymethylenepolyphenylenepolyamine (MDA) corresponding to polymethylenepolyphenylene polyisocyanate (MDI) and tolylenediamine (TDA) corresponding to tolylene diisocyanate (TDI), an aralkyl diamine, e.g., xylylenediamine (XDA) corresponding to xylylene diisocyanate (XDI) and tetramethylxylylenediamine (TMXDA) corresponding to tetramethylxylylene diisocyanate (TMXDI), an alicyclic diamine, e.g., bis(aminomethyl)norbornane (NBDA) corresponding to bis(isocyanatomethyl)norbornane (NBDI), 3-aminomethyl-3,5,5-trimethylcyclohexylamine (IPDA) corresponding to 3-isocyanatomethyl-3,5,5-trimethylcyclohexyl isocyanate (IPDI), 4,4'-methylenebis(cyclohexylamine) ($H_{12}$MDA) corresponding to 4,4'-methylenebis (cyclohexyl isocyanate) ($H_{12}$MDI), and bis(aminomethyl) cyclohexane ($H_6$XDA) corresponding to bis (isocyanatomethyl)cyclohexane ($H_6$XDI), an aliphatic dimine, e.g., hexamethylenediamine (HDA) corresponding to hexamethylene diisocyanate (HDI), and polymethylenepolyphenylpolyamine corresponding to polymethylenepolyphenyl polyisocyanate (crude MDI, polymeric MDI).

The apparatus for continuously producing polyisocyanate 1 is suitable to produce an aromatic diisocyanate using an aromatic diamine.

An organic solvent is not specifically limited as long as it can solve polyamine and polyisocyanate and is inactive thereto. Examples include an aromatic hydrocarbon, e.g., toluene and xylene, a halogenated hydrocarbon, e.g., chlorotoluene, chlorobenzene, and dichlorobenzene, esters, e.g., butyl acetate and amyl acetate, and ketones, e.g., methyl isobutyl ketone and methyl ethyl ketone. Preferably, dichlorobenzene can be used.

Then, the polyamine solution is prepared so as to be a solution of an organic solvent within a range from 5 to 50% by weight, or more preferably from 5 to 30%.

Carbonyl chloride is stored as it is or by prepared as a carbonyl chloride solution in a carbonyl chloride storage tank, and is supplied from the carbonyl chloride supplying line 10 to the material-mixing portion 8 as it is or as a carbonyl chloride solution. Further, carbonyl chloride is preferably supplied as it is or as a carbonyl chloride solution.

The carbonyl solution is prepared by dissolving carbonyl chloride ($COCl_2$) with an organic solvent. As the organic solvent, the above-described organic solvent, preferably the same organic solvent as that of the polyamine solution is used. Further, the carbonyl chloride solution is prepared as a solution of an organic solvent of 10% or more by weight of carbonyl chloride.

Further, the polyamine solution is supplied from the polyamine supplying line 9 to the material-mixing portion 8 at a supplying rate (linear velocity in a cross section of the opening portion 12 of the polyamine supplying line 9) within a range from 0.5 to 10 m/s, preferably 0.5 to 5 m/s. Further, carbonyl chloride or a solution thereof is supplied from the carbonyl chloride supplying line 10 to the material-mixing portion 8 at a supplying rate (linear velocity in a cross section of the opening portion 14 of the carbonyl chloride supplying line 10) within a range from 0.5 to 10 m/s, preferably from 0.5 to 5 m/s. Furthermore, a reaction solution supplied to the material-mixing portion 8 is supplied at a supplying rate (linear velocity of the reaction solution within the circulatory line 7 immediately before being supplied to the material-mixing portion 8) within a range from 0.3 to 5 m/s, preferably from 0.5 to 3 m/s. When each supplying rate is set to the above-described value, the yield of polyisocyanate can be more improved.

In addition, a polyamine solution, and carbonyl chloride or a carbonyl chloride solution are supplied at a stoichiometric ratio in which carbonyl chloride/polyamine is 2/1 to 60/1 (mole ratio), preferably 2/1 to 20/1 (mole ratio).

As shown in FIG. 2, in the material-mixing portion 8, a polyamine solution supplied from the polyamine supplying line 9 flows in from the opening portion 12, and carbonyl chloride or a carbonyl chloride solution flows in from the opening portion 14. Then, those contact each other in the presence of a circulating reaction solution. More particularly, a polyamine solution flowing in from the opening portion 12 of the polyamine supplying line 9 is suppressed to contact with the reaction solution circulated from the upstream side by an inner wall surface of the circulated line 7 on the one side. Further, on the other side, carbonyl chloride or a carbonyl chloride solution flows in from the opening portion 14 of the carbonyl chloride supplying line 10 toward a polyamine solution flowing in from the opening portion 12 of the polyamine supplying line 9. Thus, the polyamine solution is covered with the flowing-in carbonyl chloride or the carbonyl chloride solution so as to be suppressed to contact with the reaction solution circulated from the upstream side.

That is, since the polyamine solution supplied from the polyamine supplying line 9 is covered with the inner wall surface of the circulated line 7 and the carbonyl chloride or the carbonyl chloride solution flowing in from the opening portion 14 of the carbonyl chloride supplying line 10, the contact of the polyamine solution with the reaction solution is suppressed. Thus, the reaction of the polyisocyanate in the reaction solution and the polyamine in the supplied polyamine solution is prevented. As a result of this, the formation of a urea compound as a by-product can be suppressed, and the yield of polyisocyanate can be improved.

In the material-mixing portion 8, the supplied polyamine solution and the supplied carbonyl chloride or carbonyl chloride solution are in a state of liquid layers in which the polyamine solution is covered with the carbonyl chloride or carbonyl chloride solution as described above.

Then, in the material-mixing portion 8, the supplied polyamine solution and carbonyl chloride or carbonyl chloride solution are transported to the high-shear pump 3 with the reaction solution as shown in FIG. 1.

The polyamine solution, the carbonyl chloride or carbonyl chloride solution, and the reaction solution are substantially formed in three layers between the material-mixing portion 8 and the high-shear pump 3. Accordingly, the contact of the polyamine solution with the polyisocyanate in the reaction solution can be reduced.

In the high-shear pump 3, the supplied polyamine solution, the carbonyl chloride or carbonyl chloride solution, and the reaction solution are mixed by high shearing using the high-shearing pump 3. By this shearing, the polyamine in the polyamine solution and the carbonyl chloride or carbonyl chloride in the carbonyl chloride solution become fine liquid droplets so as to contact each other, whereby an uniform slurry of carbamoyl chloride and polyamine hydrochloride, which are hardly dissolved in an organic solvent, can be quickly produced, and the slurry is uniformly and highly dispersed in the reaction solution. Thus, within the circulatory line 7 from the high-shear pump 3 to the reactor 4, a reaction of the polyisocyanate in the reaction solution and polyamine in the supplied polyamine solution can be suppressed. Accordingly, a formation of a urea compound as a by-product can be suppressed and the yield of polyisocyanate can be improved.

Further, since the reaction solution is transported to the reactor 4 while highly dispersing the slurry, a reaction of the polyamine hydrochloride and carbonyl chloride in the solution is promoted. Further, the produced carbamoyl chloride is gradually converted to polyisocyanate.

In addition, when the reactor 4 is a first stage reactor in a multistage continuous reactor, for example, a reaction temperature is controlled to be 120° C. or lower, or preferably from 50 to 100° C.

Further, the reaction solution reacted in the reactor 4 (that is, the reaction solution containing polyisocyanate produced by the reaction, carbamoyl chloride, polyamine hydrochloride and carbonyl chloride, those of which are in a middle stage of the reaction, and an organic solvent) is partially circulated from the liquid-fed pump 5 through the circulatory line 7, and a remainder is transported to a following process (a reactor in a second stage when the reactor 4 is a first stage reactor in the multistage continuous reactor) via a transportation line 15. The transportation line 15 is not specifically limited, which transports to the following process by overflow from the reactor 4, liquid-feeding by a pressure, or taking out from a portion of the circulatory line 7 using the liquid-feeding pump 5.

The circulated reaction solution is transported to the cooler 6 by the liquid-feeding pump 5, cooled at, for example, 120° C. or lower, preferably from 50° C. to 100° C. by the cooler 6, and transported to the material-mixing portion 8 again. Then, a polyamine solution is re-supplied from the polyamine supplying line 9, and carbonyl chloride or a carbonyl chloride solution is re-supplied from the carbonyl chloride supplying line 10, in the material-mixing portion 8.

Since the reaction solution cooled by the cooler 6 flows into the material-mixing portion 8, the formation of a urea compound as a by-product can be more suppressed.

In addition, in the above-described embodiments, the high-shear pump 3 is used as a mixing means of the present invention. However, as the mixing means of the present invention, other shearing means can be used that is capable of contacting polyamine and carbonyl chloride by shearing instead of the high-shear pump 3 if the a liquid-feeding pump 5 is separately provided as described above. For example, a stirrer or a mixer can be used.

Figure 3:
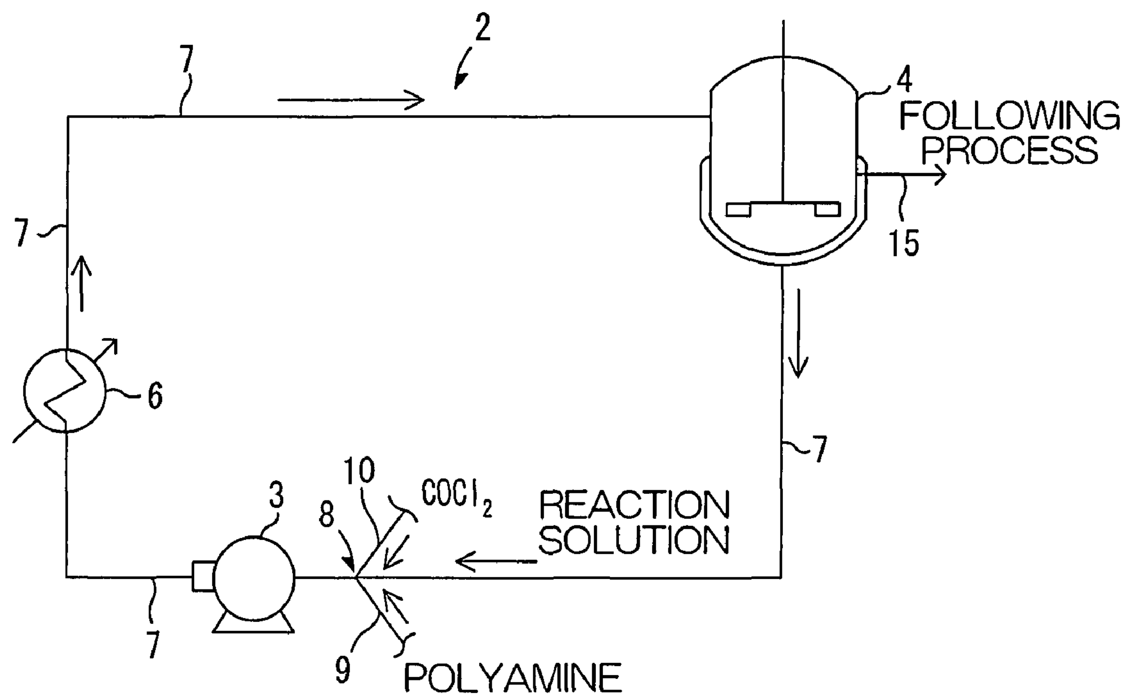
FIG. 3 is a schematic block diagram showing another embodiment of an apparatus for continuously producing polyisocyanate.

Furthermore, in the above-described embodiments, the high-shear pump 3 can work as the liquid-feeding pump 5 without providing the liquid-feeding pump 5. In this case, as shown in FIG. 3, a material-mixing portion 8 is provided at a middle position from the reactor 4 to the high-shear pump 3 in the direction of the flow of a reaction solution, and the cooler 6 is provided at a middle position from the high-shear pump 3 to the reactor 4.

INDUSTRIAL APPLICABILITY

An apparatus for continuously producing polyisocyanate of the present invention is properly used to industrially produce polyisocyanate used as a raw material of polyurethane.

The invention claimed is:

1. An apparatus for continuously producing polyisocyanate by reacting polyamine with carbonyl chloride, comprising:

a reactor and a circulatory unit for circulating a reaction solution to the reactor, the circulatory unit comprising:

1) a circulatory line for circulating the reaction solution, 2) polyamine supplying unit for supplying polyamine to the circulatory line, 3) carbonyl chloride supplying unit for supplying carbonyl chloride to the circulatory line, 4) polyamine-carbonyl chloride contacting unit for contacting the polyamine supplied from the polyamine supplying unit to the circulatory line and the carbonyl chloride supplied from the carbonyl chloride supplying unit to the circulatory line in the presence of the circulating reaction solution, and 5) mixing unit for mixing the carbonyl chloride and the polyamine contacted by the contacting unit, and the circulated reaction solution by shearing, wherein the polyamine supplied from the polyamine supplying unit, the carbonyl chloride supplied from the carbonyl supplying unit, and the reaction solution substantially form three layers from the contacting unit to the mixing unit.

2. The apparatus for continuously producing polyisocyanate according to claim 1, wherein the polyamine supplied from the polyamine supplying unit to the circulatory line and the polyisocyanate in the circulated reaction solution are not substantially reacted in the circulatory unit.

3. The apparatus for continuously producing polyisocyanate according to claim 1, wherein a distance between the contacting unit and the mixing unit is 1,000 mm or less.

4. The apparatus for continuously producing polyisocyanate according to claim 1, wherein a linear velocity of the polyamine supplied from the polyamine supplying unit to the circulatory line is from 0.5 to 10 m/sec in a cross section of the polyamine supplying unit, a linear velocity of the carbonyl chloride supplied from the carbonyl chloride supplying unit to the circulatory line is from 0.5 to 10 m/sec in a cross section of the carbonyl chloride supplying unit, and a linear velocity of the reaction solution within the circulatory line immediately before supplying to the contacting unit is from 0.3 to 5 m/sec.

5. The apparatus for continuously producing polyisocyanate according to claim 1, wherein a cooling device is interposed in a middle of the circulatory line, and a temperature of the reaction solution after supplying the polyamine and the carbonyl chloride within the circulatory line is controlled to 120° C. or lower.

6. An apparatus for continuously producing polyisocyanate by reacting polyamine with carbonyl chloride, comprising:

a reactor and a circulatory unit for circulating a reaction solution to the reactor, the circulatory unit comprising:

1) a circulatory line for circulating the reaction solution, 2) polyamine supplying unit for supplying polyamine to the circulatory line, 3) carbonyl chloride supplying unit for supplying carbonyl chloride to the circulatory line, 4) polyamine-carbonyl chloride contacting unit for contacting the polyamine supplied from the polyamine supplying unit to the circulatory line and the carbonyl chloride supplied from the carbonyl chloride supplying unit to the circulatory line in the presence of the circulating reaction solution, and 5) mixing unit for mixing the carbonyl chloride and the polyamine contacted by the contacting unit, and the circulated reaction solution by shearing, wherein the polyamine supplying unit comprises a polyamine supplying line having an flow-out side end portion that is inserted into the circulatory line, the carbonyl chloride supplying unit comprises a carbonyl chloride supplying line having a flow-out side end portion that is inserted into the circulatory line, the flow-out side end portion of the polyamine supplying line is provided adjacent to an inner wall surface of the circulatory line, and opens toward the downstream side with respect to the flow of the reaction solution from the contacting unit to the mixing unit, and the flow-out side end portion of the carbonyl chloride supplying line opens toward a flow-out solution of the polyamine supplied from the flow-out side end portion of the polyamine supplying line.

7. The apparatus for continuously producing polyisocyanate according to claim 6, wherein the polyamine supplied from the polyamine supplying unit to the circulatory line and the polyisocyanate in the circulated reaction solution are not substantially reacted in the circulatory unit.

8. The apparatus for continuously producing polyisocyanate according to claim 6, wherein a distance between the contacting unit-and the mixing unit is 1,000 mm or less.

9. The apparatus for continuously producing polyisocyanate according to claim 6, wherein a linear velocity of the polyamine supplied from the polyamine supplying unit to the circulatory line is from 0.5 to 10 m/sec in a cross section of the polyamine supplying unit, a linear velocity of the carbonyl chloride supplied from the carbonyl chloride supplying unit to the circulatory line is from 0.5 to 10 m/sec in a cross section of the carbonyl chloride supplying unit, and a linear velocity of the reaction solution within the circulatory line immediately before supplying to the contacting unit is from 0.3 to 5 m/sec.

10. The apparatus for continuously producing polyisocyanate according to claim 6, wherein a cooling device is interposed in a middle of the circulatory line, and a temperature of the reaction solution after supplying the polyamine and the carbonyl chloride within the circulatory line is controlled to 120° C. or lower.

* * * * *